United States Patent [19]

Nakamura et al.

[11] Patent Number: 4,794,148

[45] Date of Patent: Dec. 27, 1988

[54] FIBER-REINFORCED COMPOSITE MATERIAL

[75] Inventors: Hiroshi Nakamura; Shigenao Hata, both of Niihama; Kunimasa Kamio, Suita; Yasuhisa Saito, Higashiosaka, all of Japan

[73] Assignee: Sumitomo Chemical Company, Limited, Osaka, Japan

[21] Appl. No.: 144,426

[22] Filed: Jan. 15, 1988

[30] Foreign Application Priority Data

Jan. 28, 1987 [JP] Japan ................................. 62-19265

[51] Int. Cl.⁴ .......................................... C08F 283/10
[52] U.S. Cl. .................................... 525/530; 525/533; 525/423; 525/523; 525/397
[58] Field of Search ............... 525/530, 533, 423, 523, 525/397

[56] References Cited

U.S. PATENT DOCUMENTS 4,273,916  6/1981  Jones ................................... 525/397
4,510,272  4/1985  Loszewski ........................... 525/530

FOREIGN PATENT DOCUMENTS 2270055  9/1985  Fed. Rep. of Germany ...... 525/530

OTHER PUBLICATIONS

Chemical Abstract 108(4):22481h, Heat-Curable Imide Compounds, Saito et al., (1988).
Indian J. of Chemistry, vol. 20B Sep. 1981, pp. 755-758, Diels-Alder Reaction: 1,4-Cyclo Addition of N-Aryl-Maleimides to Alkylidiene & Arlidene-Fluorenones & Synthesis of Some New Fluoranthene Deriv., Abdow et al.

Primary Examiner—John C. Bleutge
Assistant Examiner—Annabel Y. Lee
Attorney, Agent, or Firm—Wenderoth, Lind & Ponack

[57] ABSTRACT

A fiber-reinforced composite material superior in mechanical strength, heat resistance and hot water resistance is provided herein. This composite material is composed of a matrix of a cured product of a resin composition containing as essential components an epoxy resin (A) and an imide compound (B) represented by the following general formula (I),

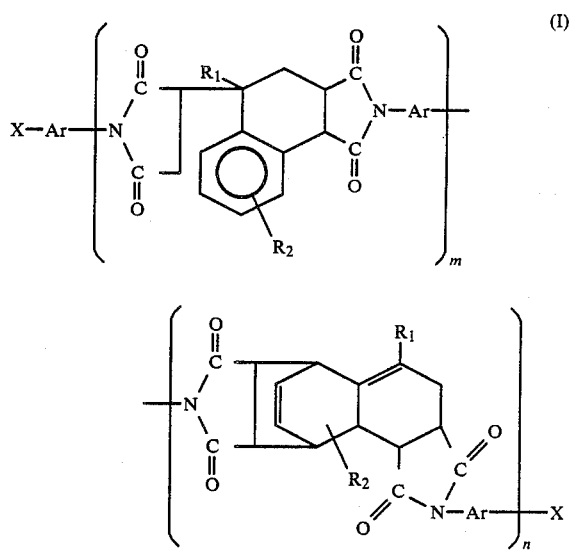

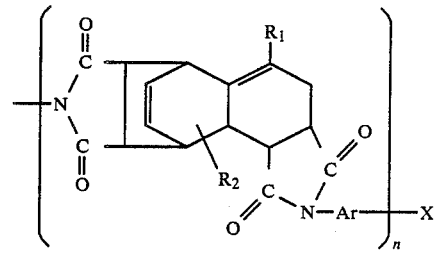

wherein X represents —NH$_2$ group and/or —OH group, Ar represents an aromatic residue, R$_1$ represents a hydrogen atom or an alkyl group having from 1 to 10 carbon atoms, R$_2$ represents a hydrogen atom, an alkyl or alkoxy group having from 1 to 20 carbon atoms or a hydroxyl group, and each of m and n cannot be 0 at the same time, and a fiber (C) as a reinforcing material.

3 Claims, No Drawings

FIBER-REINFORCED COMPOSITE MATERIAL

The present invention relates to a fiber-reinforced composite material superior in mechanical strength, heat resistance and hot water resistance.

Composite materials with fibers as a reinforcing material have a large tensile strength and a large modulus of elasticity, and they are finding extending uses as structural materials for airplanes and automobiles, component parts of engines, sporting goods, goods for leisure time amusement, etc.

For a material for the matrix phase of these composite materials, thermosetting resins, particularly epoxy resins have mainly been used in terms of moldability and mechanical properties.

In recent years, however, with extension of the application field of composite materials, materials have come to be desired which have more improved mechanical strength than they have had before and maintain chemical stability and mechanical properties even under severe environments such as environments of higher temperature and higher humidity than in the conventional environments of use.

In fiber-reinforced composite materials, in order that the reinforcing fiber may exhibit its characteristics to the maximum, a resin used as a matrix is important. In order to answer the above demand, improvement in the matrix resin is necessary.

An object of the present invention is to provide a composite material superior in mechanical strength, heat resistance and hot water resistance.

The present invention provides a fiber-reinforced composite material comprising a matrix composed of a cured product of a resin composition containing as essential components an epoxy resin (A) and an imide compound (B) represented by the following general formula (I),

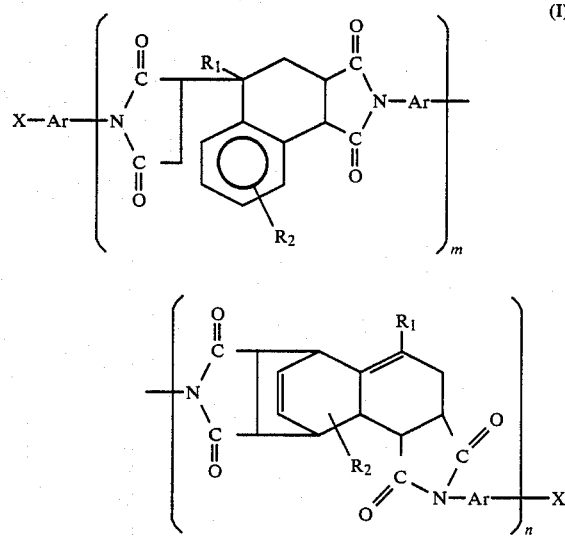

wherein Ar represent an aromatic residue, $R_1$ represents a hydrogen atom or an alkyl group having from 1 to 10 carbon atoms, $R_2$ represents a hydrogen atom, an alkyl or alkoxy group having from 1 to 20 carbon atoms or a hydroxyl group, X represents an $-NH_2$ group and/or $-OH$ group, and each of m and n represents a number of from 0 to 30, preferably from 0 to 8, more preferably from 0 to 4, provided that m and n are not zero at the same time, and a fiber (C) as a reinforcing material.

As a result of a study in view of the above situation, the present inventors have found that a fiber-reinforced composite material obtained with the aforementioned epoxy resin composition as a matrix phase and a fiber as a reinforcing material is superior in mechanical strength, heat resistance and hot water resistance. The present invention has been completed in this way.

The present invention will be illustrated in more detail.

The epoxy resin (A) used in the present invention is a compound having two or more epoxy groups in the molecule. Examples of the epoxy resin include glycidyl ether compounds derived from dihydric or more phenols [e.g. bisphenol A, bisphenol F, hydroquinone, resorcinol, phloroglucinol, tris(4-hydroxyphenyl)methane, 1,1,2,2-tetrakis(4-hydroxyphenyl)ethane] or halogenated bisphenols e.g. tetrabromobisphenol A); novolak type epoxy resins derived from novolak resins which are reaction products of phenols (e.g. phenol, o-cresol) with formaldehyde; amine type epoxy resins derived from aniline, p-aminophenol, m-aminophenol, 4-amino-m-cresol, 6-amino-m-cresol, 4,4'-diaminodiphenylmethane, 3,3'-diaminodiphenylmethane, 4,4'-diaminodiphenyl ether, 3,4'-diaminodiphenyl ether, 1,4-bis(4-aminophenoxy)benzene, 1,4-bis(3-aminophenoxy)benzene, 1,3-bis(4-aminophenoxy)benzene, 1,3-bis(3-aminophenoxy)benzene, 2,2-bis(4-aminophenoxyphenyl)propane, p-phenylenediamine, m-phenylenediamine, 2,4-tolylenediamine, 2,6-tolylenediamine, p-xylylenediamine, m-xylylenediamine, 1,4-cyclohexane-bis(methylamine), 1,3-cyclohexane-bis(-methylamine), 5-amino-1-(4'-aminophenyl)-1,3,3-trimethylindane, 6-amino-1-(4'-aminophenyl)-1,3,3-trimethylindane, etc.; glycidyl ester compounds derived from aromatic carboxylic acids (e.g. p-oxybenzoic acid, m-oxybenzoic acid, terephthalic acid, isophthalic acid); hydantoin type epoxy resins derived from 5,5-dimethylhydantoin, etc.; alicyclic epoxy resins such as 2,2'-bis(3,4-epoxycyclohexyl)propane, 2,2-bis[4-(2,3-epoxypropyl)cyclohexyl]propane, vinylcyclohexene dioxide, 3,4-epoxycyclohexylmethyl-3,4-epoxycyclohexanecarboxylate, etc.; and other compounds such as triglycidyl isocyanulate, 2,4,6-triglycidoxy-S-triazine, etc. These epoxy resins may be used alone or in combination.

Next, the imide compound (B) will be illustrated.

Referring more particularly to Ar in the foregoing formula (I), Ar is a mononuclear or polynuclear divalent aromatic residue of which the aromatic ring may or may not be substituted with a lower alkyl group, a halogen atom, a lower alkoxy group, etc. Specifically, one or more of aromatic amine residues may be given as Ar. More specifically, when the terminal group X is $-NH_2$, Ar is an aromatic diamine residue, and when the terminal group X is $-OH$, Ar adjacent to the terminal group is an aminophenol residue and other Ars are an aromatic diamine residue.

For examples of the aromatic diamine there may be given one or more of 4,4'-diaminodiphenylmethane, 3,3'-diaminodiphenylmethane, 4,4'-diaminodiphenyl ether, 3,4'-diaminodiphenyl ether, 4,4'-diaminodiphenylpropane, 4,4'-diaminodiphenyl sulfone, 3,3'diaminodiphenyl sulfone, 2,4-tolylenediamine, 2,6-tolylenediamine, m-phenylenediamine, p-phenylenediamine, benzidine, 4,4'-diaminodiphenyl sulfide, 3,3'-dichloro-4,4'-diaminodiphenyl sulfone, 3,3'-dichloro- 4,4'-diaminodiphenylpropane, 3,3'-dimethyl-4,4'-diaminodiphenylmethane, 4,4'-methylene-bis(2-ethyl-6-methylaniline), 4,4'-methylene-bis(2,6-diethylaniline), 4,4'-methylene-bis(2,6-diisopropylaniline), 4,4'-methylene-bis(2-isopropyl-6-methylaniline), 3,3'-dimethoxy-4,4' diaminobiphenyl, 3,3'-dimethyl-4,4'-diaminobiphenyl, 1,3-bis(4-aminophenoxy)benzene, 1,3-bis(3-aminophenoxy)benzene, 1,4-bis(4-aminophenoxy)benzene, 2,2-bis(4-aminophenoxyphenyl)propane, 4,4'-bis 4-aminophenoxy)diphenyl sulfone, 4,4'-bis(3-aminophenoxy)diphenyl sulfone, 9,9'-bis(4-aminophenyl)fluorene, 3,3'-dicarboxy-4,4'-diaminodiphenylmethane, 2,4-diaminoanisole, bis(3-aminophenyl)methylphosphine oxide, 3,3'-diaminobenzophenone, o-toluidine sulfone, 4,4'-methylene-bis-o-chloroaniline, tetrachlorodiaminodiphenylmethane, m-xylylenediamine, p-xylylenediamine, 4,4'-diaminostilbene, 5-amino-1-(4'-aminophenyl)-1,3,3-trimethylindane, 6-amino-1-(4'-aminophenyl)1,3,3-trimethylindane, 5-amino-6-methyl-1-(3'-amino-4'-methylphenyl)1,3,3-trimethylindane, 7-amino-6-methyl-1-(3'-amino-4'-methylphenyl)1,3,3-trimethylindane, 6-amino-5-methyl-1-(4'-amino-3'-methylphenyl)1,3,3-trimethylindane, 6-amino-7-methyl-1-(4'-amino-3'-methylphenyl)1,3,3-trimethylindane, etc.

On the other hand, for examples of the aminophenol, there may be given one or more of o-aminophenol, m-aminophenol, p-aminophenol, 6-amino-m-cresol, 4-amino-m-cresol, 2,2-(4-hydroxyphenyl-4-aminophenyl)propane, 2,2-(4-hydroxyphenyl-2'-methyl-4'-aminophenyl)propane, 2,23-methyl-4-hydroxyphenyl-4'-aminophenyl)propane, 3-amino-1-naphthol, 8-amino-2-naphthol, 5-amino-1-naphthol, 4-amino-2-methyl-1-naphthol, etc.

$R^1$ and $R^2$ are as defined above, and $R^1$ is preferably an alkyl group having from 1 to 10 carbon atoms, more preferably an alkyl group having from 1 to 3 carbon atoms. $R_2$ is preferably a hydrogen atom, an alkyl or alkoxy group having from 1 to 20 carbon atoms or a hydroxyl group, more preferably a hydrogen atom, an alkyl or alkoxy group having from 1 to 5 carbon atoms or a hydroxyl group.

A method to produce the functional group-terminated imide compound (B) of the present invention will be illustrated.

Those in which X in the formula (I) is —NH$_2$ may be synthesized by reacting an excess of the foregoing aromatic diamine with a compound represented by the general formula,

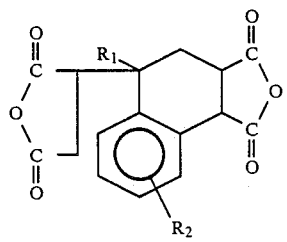

and/or

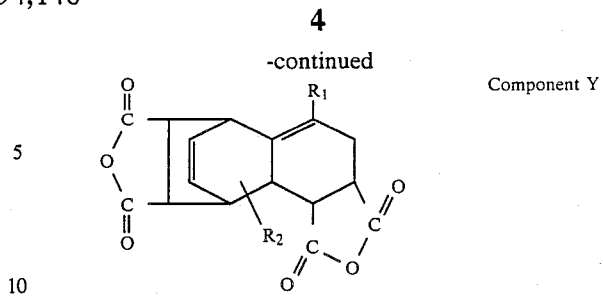

Component Y wherein $R_1$ and $R_2$ are as defined above, (hereinafter referred to as $B_1$, and the isomers are referred to as component X and component Y, respectively) according to the common imidation technique. The compound thus synthesized is taken as $B_2$.

Those in which X in the formula (I) is —OH may be synthesized by adding the foregoing aromatic monoamine having an —OH group and aromatic diamine to $B_1$ so that the molar ratio of the aromatic diamine to $B_1$ is (m+n) to (m+n+1), and besides the molar ratio of the aromatic monoamine to $B_1$ is 2 to (m+n+1) (wherein m and n are as defined above), and carrying out reaction according to the common imidation technique.

A method to synthesize the functional group-terminated imide compound of the present invention has been illustrated above, but the method is not of course limited thereto.

$B_1$ can be synthesized by the known method. For example, $B_1$ is obtained by reacting a compound represented by the general formula,

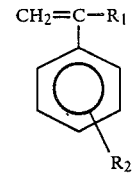

wherein $R_1$ and $R_2$ are as defined above, (hereinafter referred to as $B_3$) with maleic anhydride at a former to latter molar ratio of 1 to 2 in the absence of a radical polymerization catalyst and in the presence or absence of a radical polymerization inhibitor. Examples of $B_3$ include one or more of styrene, α-methylstyrene, α,p-dimethylstyrene, α,m-dimethylstyrene, isopropylstyrene, vinyltoluene, p-tert-butylstyrene, p-isopropenylphenol, m-isopropenylphenol, 1-methoxy-3-isopropenylbenzene, 1-methoxy-4-isopropenylbenzene, vinylxylene, etc.

The functional group-terminated imide compounds of the present invention thus obtained are soluble in high concentrations in low-boiling solvents such as acetone, methyl ethyl ketone, methyl isobutyl ketone, methyl cellosolve, ethyl cellosolve, methylene chloride, chloroform, etc, and also they are superior in compatibility with epoxy resins.

The resin composition of the present invention contains the aforementioned epoxy resin and functional group-terminated imide compound as essential components, and if necessary, it may contain other additives such as the known epoxy resin curing agents, curing accelerators, fillers, flame retardants, reinforcing agents, surface-treating agents, pigments, etc.

The known epoxy resin curing agents include amine type curing agents such as aromatic amines (e.g. xylylenediamine) and aliphatic amines, polyphenol compounds such as phenol novolak and cresol novolak, acid anhydrides, dicyandiamide, hydrazide compounds, etc. As to the proportion of the epoxy resin (A) and functional group-terminated imide compound (B), the sum of (B) and other curing agents is from 0.8 to 1.2 gram equivalent per 1 gram equivalent of (A), and preferably the amount of (B) is 0.02 gram equivalent or more per 1 gram equivalent of the same.

The curing accelerators include amines [e.g. benzyldimethylamine, 2,4,6-tris(dimethylaminomethyl)-phenol, 1,8-diazabicycloundecene], imidazole compounds (e.g. 2-ethyl-4-methylimidazole), boron trifluoride amine complexes, etc.

The fiber used as a reinforcing material in the present invention includes inorganic or organic fibers having a tensile strength of 0.5 GPa or more and a Young's modulus of elasticity of 50 GPa or more such as carbon fibers, graphite fibers, glass fibers, silicon carbide fibers, alumina fibers, titania fibers, boron nitride fibers, aromatic polyamide fibers, aromatic polyester fibers, polybenzimidazole fibers, etc. These fibers may be used in the form of continuous tow, woven fabric, short fiber, whisker, etc.

Also, depending upon the object of use, two or more kinds of fiber or fibers of different forms may be used in combination. Further, incorporating the granular products of talc, mica, calcium carbonate, alumina hydrate, silicon carbide, carbon black, silica, etc. in addition to the reinforcing fiber is also effective to improve the viscosity of the resin composition, thereby facilitating molding of the composite material, or to improve the mechanical properties such as compression strength, etc. of the composite material obtained.

For a method to produce the composite material, any of the conventionally known methods for producing fiber-reinforced composite materials with an epoxy resin as a matrix, for example a prepreg method, filament winding method, resin injection molding method, etc. can be used, but the prepreg method is suitable. The term "prepreg" referred to herein means reinforcing fibers impregnated with a resin composition, and the prepreg may take any form of sheet, continuous tow, strand, yarn and pellet. The sheet-form prepreg takes a form in which reinforcing fibers have been drawn out in the form of continuous tow, a form in which short fibers have been tangled in the form of mat, or a form of woven fabric. Also, laminated sheet-form prepregs in which several pieces of sheet different in structure have been piled up, and those in which several pieces of continuous tow prepreg have been bundled, are a useful material.

The fiber content of these prepregs is generally from 5 to 70% by volume, particularly preferably from 10 to 60% by volume.

After laminating or winding these prepregs into a desired form, by curing the resin composition by applying heat and pressure, a fiber-reinforced composite material can be obtained.

The fiber-reinforced composite material of the present invention is superior in mechanical strength, heat resistance and hot water resistance, and useful as a structural material.

The present invention will be illustrated in more detail with reference to the following examples.

Hereupon, the followings were synthesized as a material for synthesizing the functional group-terminated imide oligomer by the method given above.

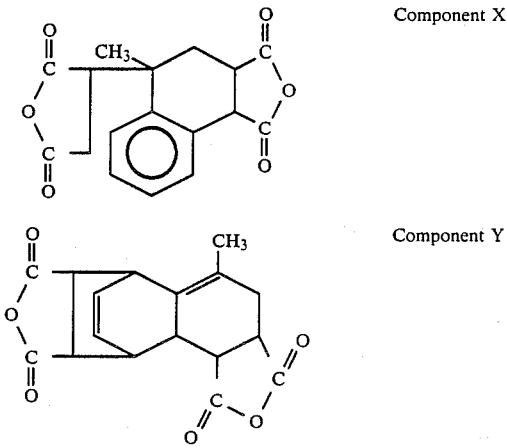

Component X

Component Y

REFERENCE EXAMPLE 1

To a flask equipped with a stirrer, thermometer and separater were added 29.7 g (0.15 mole) of 4,4'-diaminodiphenylmethane and 242 g of m-cresol, and after dissolving the diaminodiphenylmethane, 48.5 g of xylene was added. The temperature was raised to 120° C. At this temperature, 31.4 g (0.1 mole) of Component X was added, and after raising the temperature to 175° C., dehydration was continued for 5 hours. After completion of the reaction, the reaction solution was poured into a hexane/isopropanol mixed solvent, and formed precipitates were filtered, washed twice with the same solution and dried under reduced pressure to obtain an imide compound. The melting point of this compound was about 240° C., and the amine equivalent thereof was 643 g/eq.

REFERENCE EXAMPLE 2

An imide compound was obtained in the same manner as in Reference example 1 except that 29.7 g (0.15 mole) of 4,4'-diaminodiphenylmethane was replaced by 24.4 g (0.2 mole) of 2,4-tolylenediamine. The melting point of this compound was about 220° C., and the amine equivalent thereof was 353 g/eq.

REFERENCE EXAMPLE 3

To a flask equipped with a stirrer, thermometer and separater were added 80.2 g (0.27 mole) of m-aminophenol and 312 g of mm-cresol, and after dissolving m-aminophenol, 62.2 g of xylene was added. The temperature was raised to 120° C. At this temperature, 110 g 0.35 mole) of Component X was added, and an imide compound was obtained by the same procedure as in Reference example 1. The melting point of this compound was 300° C., and the hydroxyl equivalent thereof was 239 g/eq.

REFERENCE EXAMPLE 4

In the same manner as in Reference example 3, 64 g (0.20 mole) of Component X and 230.2 g of m-cresol were charged, and after dissolving Component X, the temperature was raised to 70° C.; at this temperature, 12.4 g (0.1 mole) of 2,4-tolylenediamine was added, and after maintaining the temperature for 1 hour, 22.2 g (0.20 mole) of m-aminophenol was added; after maintaining the temperature for further 1 hour, 46 g of xylene was added, the temperature was raised to 175° C., and dehydration was continued for 5 hours. Thereafter, an imide compound was obtained by the same procedure as in Reference example 3. The melting point of this compound was 260° C., and the hydroxyl equivalent thereof was 426 g/eq.

REFERENCE EXAMPLE 5

To a flask equipped with a stirrer, thermometer and separator were added 26.2 g (0.215 mol) of 2,4-tolylenediamine and 117 g of m-cresol, and after raising the temperature to 70° C. to dissolve 2,4-tolylenediamine, 20.3 g (0.064 mole) of Component X and 24.7 g (0.079 mole) of Component Y were charged to form a polyamide acid. Thereafter, 25.2 g of toluene was added, and after raising the temperature to 150° C., dehydration was continued at the same temperature for 10 hours. After completion of the reaction, the resin solution obtained was poured into 750 g of isopropanol, and formed precipitates were filtered off, washed twice and dried under reduced pressure to obtain an imide compound. The melting point of this compound was 260° C., and the amine equivalent thereof was 498 g/eq.

REFERENCE EXAMPLE 6

To a flask equipped with a stirrer, thermometer and separator were added 20.3 g (0.064 mole) of Component X, 24.7 g (0.079 mole) of Component Y, 161 g of m-cresol and 8.68 g (0.0714 mole) of 2,4-tolylenediamine, and reaction was carried out at a temperature of 70° C. for 1 hour. Thereafter, 32.2 g of xylene was charged, and dehydration was continued at a temperature of 170° C. for 6 hours.

After completion of the reaction, 550 g of the resulting resin solution was poured into isopropanol, and formed precipitates were filtered off, washed twice and dried under reduced pressure to obtain an imide compound. The hydroxyl equivalent of this compound was 473 g/eq, and the melting point thereof was 270° C.

REFERENCE EXAMPLE 7

An imide compound was obtained in the same manner as in Reference example 6 except that the amount of Component X was changed to 5.4 g (0.024 mole), that of Component Y was changed to 26.6 g 0.119 mole), 8.68 g (0.071 mole) of 2,4-tolylenediamine was replaced by 12 g (0.064 mole) of 4,4'-diaminodiphenylmethane and the amount of m-aminophenol was changed from 15.5 g (0.14 mole) to 8.30 g (0.076 mole). The hydroxyl equivalent of this compound was 702 g/eq, and the melting point thereof was about 270° C.

REFERENCE EXAMPLE 8

An imide compound was obtained in the same manner as in Reference example 5 except that 29.7 g (0.094 mole) of Component X and 15.3 g (0.049 mole) of Component Y were charged. The amine equivalent of this compound was 506 g/eq, and the melting point thereof was about 260° C.

EXAMPLES 1 to 4

Sumi ® epoxy ELA-128 (bisphenol A type epoxy resin having an epoxy equivalent of 187 g/eq; product of Sumitomo Chemical Co., Ltd.) and the imide compounds obtained in Reference examples 1, 2, 5 and 7 were blended in proportions shown in Table 1 and dissolved in acetone to obtain about 50% by weight resin solutions. These resin solutions were taken as a resin solution for prepreg.

A carbon fiber (Magnamite ® AS 4; product of Sumika Hercules Co., Ltd.) was passed through said resin solution for prepreg to impregnate it with the resin and rolled round a silicon release paper, as previously wound on a drum, from one side to the other side of the drum while moving the drum. The amount of the resin attached to the carbon fiber was regulated by passing the fiber between two stainless steel rods freely adjustable in a gap therebetween. The resulting roll of fiber round the silicon release paper was cut across the surface of the drum and removed from the drum to obtain a carbon fiber sheet. This sheet was placed for 30 minutes in an explosion-proof hot air oven previously set to a temperature of 120° C. to carry out solvent removal and B-stage which is pre-treatment for the complete curing of the resin impregnated into the fiber. The carbon fiber sheet thus prepared was taken as a prepreg. Every prepreg thus obtained contained about 35% by weight of the resin and its fiber weight was 150 g/m$^2$. The prepreg was cut, laminated and matched die molded by means of a hot press. The temperature of the mold was adjusted to 180° C. Thereafter, the molded product was taken off the mold and cured at a temperature of 200° C. in 4 hours to obtain a unidirectional composite material containing 60% by volume of the carbon fiber. The samples thus obtained were measured for mechanical properties. The results are shown in Table 1.

COMPARATIVE EXAMPLE 1

A one-way reinforced composite material was obtained in the same manner as in Example 1 except that 30 g of Sumicure ® S (diaminodiphenyl sulfone; product of Sumitomo Chemical Co., Ltd.) was used in place of the imide compound obtained in Reference example 1. The sample thus obtained was measured for mechanical properties. The results are shown in Table 1.

TABLE 1

| | | | Example 1 | Example 2 | Example 3 | Example 4 | Comparative example 1 |
|---|---|---|---|---|---|---|---|
| Composition | Sumi ® epoxy ELA-128 (g) | | 100 | 100 | 100 | 100 | 100 |
| | Imide compound in Reference example 1 (g) | | 136 | — | — | — | — |
| | Imide compound in Reference example 2 (g) | | — | 75 | — | — | — |
| | Imide compound in Reference example 5 (g) | | — | — | 105 | — | — |
| | Imide compound in Reference example 8 (g) | | — | — | — | 107 | — |
| | Sumicure ® S (g) | | — | — | — | — | 26 |
| Mechanical properties of composite material | Interlaminar shear strength (kg/mm$^2$) | Room temperature | 12.5 | 11.9 | 12.8 | 12.2 | 9.3 |
| | | 120° C. | 6.0 | 6.2 | 6.1 | 6.3 | 4.0 |
| | | 120° C. (wet)* | 4.3 | 4.1 | 4.5 | 4.2 | 2.1 |
| | 0° Flexural | Room temperature | 210 | 213 | 221 | 216 | 214 |

TABLE 1-continued

| | | Example 1 | Example 2 | Example 3 | Example 4 | Comparative example 1 |
|---|---|---|---|---|---|---|
| strength (kg/mm²) | 120° C. | 138 | 143 | 140 | 138 | 100 |
| | 120° C. (wet)* | 113 | 117 | 116 | 115 | 66 |
| 90° Flexural strength (kg/mm²) | Room temperature | 12.5 | 12.1 | 13.0 | 12.4 | 10.1 |

Measuring method:
Interlaminar shear strength ... according to ASTM D-2344
Flexural strength ... according to ASTM D-790
*Measurement value after dipping in boiling water for 48 hours.

EXAMPLES 5 to 9

Sumi® epoxy ELM-434 (tetraglycidyldiaminodiphenylmethane having an epoxy equivalent of 120 g/eq; product of Sumitomo Chemical Co., Ltd.), the imide compounds obtained in Reference examples 2, 3, 4, 6 and 7 and Sumicure® M (diaminodiphenylmethane; product of Sumitomo Chemical Co., Ltd.) were blended in proportions shown in Table 2 and dissolved in acetone to obtain about 50% by weight resin solutions. These resin solutions were taken as a resin solution for prepreg.

In the same manner as in Example 1, prepregs were prepared, molded and cured to obtain unidirectional composite materials containing 60% by volume of the carbon fiber, and the mechanical properties of the materials were measured. The results are shown in Table 2.

COMPARATIVE EXAMPLE 2

100 Grams of Sumi® epoxy ELM 434 (same as in Example 3( and 40 g of Sumicure® S (same as in Comparative example 1) were dissolved in 150 g of acetone to obtain a uniform solution. Using this resin solution, a fiber-reinforced composite material was obtained in the same manner as in Example 1, and the mechanical properties of the material were measured. The results are shown in Table 2.

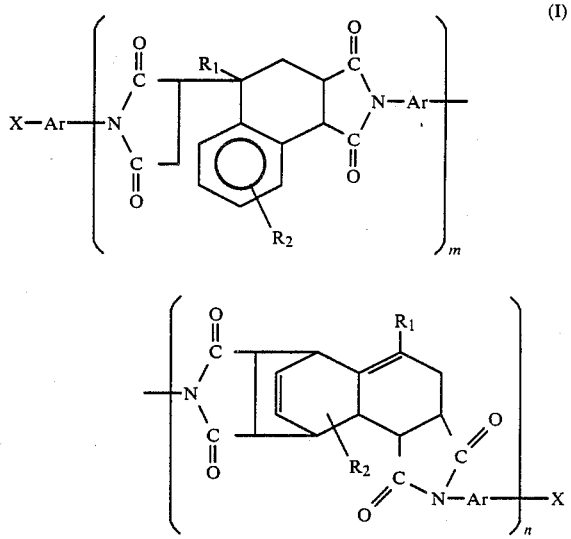

wherein X represents $-NH_2$ group and/or $-OH$ group, Ar represents an aromatic residue, $R_1$ represents a hydrogen atom or an alkyl group having from 1 to 10 carbon atoms, $R_2$ represents a hydrogen atom, an alkyl or alkoxy group having from 1 to 20 carbon atoms or a hydroxyl group, and each of m and n represents a number of from 0 to 30, provided that m and n cannot be 0 at the same time, and a fiber (C) as a reinforcing material.

2. A fiber-reinforced composite material according to claim 1 wherein $R_1$ in the formula for the imide compound (B) is an alkyl group having from 1 to 10 carbon atoms.

3. A fiber-reinforced composite material according to claim 1 wherein X in the formula for the imide compound (B) is $-NH_2$ group.

TABLE 2

| | | | Example 5 | Example 6 | Example 7 | Example 8 | Example 9 | Comparative example 2 |
|---|---|---|---|---|---|---|---|---|
| Composition | Sumi ® epoxy ELM 434 (g) | | 100 | 100 | 100 | 100 | 100 | 100 |
| | Imide compound in Reference example 2 (g) | | 100 | — | — | — | — | — |
| | Imide compound in Reference example 3 (g) | | — | 100 | — | — | — | — |
| | Imide compound in Reference example 4 (g) | | — | — | 100 | — | — | — |
| | Imide compound in Reference example 6 (g) | | — | — | — | 100 | — | — |
| | Imide compound in Reference example 7 (g) | | — | — | — | — | 100 | — |
| | Sumicure ® M (g) | | 5 | 11 | 20 | 21 | 24 | — |
| | Sumicure ® S (g) | | — | — | — | — | — | 40 |
| Mechanical properties of composite material | Interlaminar shear strength (kg/mm²) | Room temperature | 13.2 | 12.9 | 13.3 | 13.0 | 12.7 | 12.5 |
| | | 120° C. | 9.0 | 9.1 | 8.7 | 8.9 | 9.0 | 8.3 |
| | | 120° C. (wet)* | 7.0 | 6.3 | 6.5 | 6.2 | 6.8 | 3.1 |
| | | 180° C. | 7.2 | 7.7 | 7.6 | 7.5 | 7.6 | 5.6 |
| | 0° Flexural strength (kg/mm²) | Room temperature | 215 | 221 | 213 | 206 | 218 | 213 |
| | | 120° C. | 173 | 175 | 171 | 176 | 171 | 149 |
| | | 120° C. (wet)* | 148 | 139 | 145 | 142 | 139 | 109 |
| | | 180° C. | 166 | 156 | 152 | 168 | 161 | 128 |

Measuring method: Same as in Table 1.
*Same as in Table 1

What is claimed is:

1. A fiber-reinforced composite material comprising a matrix of a cured product of a resin composition containing as essential components an epoxy resin (A) and an imide compound (B) represented by the following general formula (I),